United States Patent [19]

Hagarty

[11] Patent Number: 4,889,710

[45] Date of Patent: Dec. 26, 1989

[54] AEROSOL FOAM BAIT INSECTICIDE

[75] Inventor: John D. Hagarty, Racine County, Wis.

[73] Assignee: S. C. Johnson & Son, Inc., Racine, Wis.

[21] Appl. No.: 922,926

[22] Filed: Oct. 24, 1986

Related U.S. Application Data

[63] Continuation of Ser. No. 727,932, Apr. 26, 1985, abandoned.

[51] Int. Cl.$^4$ ............................................. A01N 25/06
[52] U.S. Cl. ........................................ 424/45; 424/84
[58] Field of Search ...................................... 424/45, 84

[56] References Cited

U.S. PATENT DOCUMENTS

| | | | |
|---|---|---|---|
| 3,524,911 | 8/1970 | Leavitt | 424/45 |
| 3,816,610 | 6/1974 | Lusby | 424/84 |
| 3,970,584 | 7/1976 | Hart et al. | 424/45 |
| 4,286,020 | 8/1981 | Himel et al. | 428/407 |
| 4,456,587 | 6/1984 | Keith | 424/84 |

FOREIGN PATENT DOCUMENTS

| | | | |
|---|---|---|---|
| 0064601 | 4/1982 | Japan | 424/84 |
| 1107140 | 3/1968 | United Kingdom | 424/45 |

*Primary Examiner*—Alan L. Rotman
*Assistant Examiner*—Zinna Northington-Davis

[57] ABSTRACT

Aerosol stable foam insecticide bait composition suitable for crawling insects which comprises a film forming edible foam carrier, an attractant suitable to be carried by the foam and a toxicant which should be non-repellent, is disclosed. The foam is comprised of a film forming water soluble polymer which contains an emulsifier. The composition is formulated so that it can be pressurized within a container. Upon release into a crevice, the foam expands and coats the entire intersurface, then contracts upon drying to present a passageway for the insects to contact the toxicant. The film forming polymer may be of an edible nature such that social insects such as ants will carry away pieces of the edible foam carrier into their nests where it will be fed to others within the colony thereby controlling or eradicating the colony.

8 Claims, No Drawings

1

AEROSOL FOAM BAIT INSECTICIDE

REFERENCE TO RELATED APPLICATION

This application is a continuation of patent application Ser. No. 727,932, filed Apr. 26, 1985, now abandoned, the benefit of which is now claimed for purposes of priority pursuant to 34 U.S.C. §120.

BACKGROUND OF THE INVENTION

This invention relates to an aerosol stable foam insect bait composition for crawling insects which presents an edible foam matrix which is water soluble and which carries a toxicant having either delayed toxicity or immediate effect when the insect come in contact with the toxicant, either by crawling over the bait of the present invention or by ingesting it.

This invention also relates to an aerosol stable foam insecticidal bait composition which is useful in controlling social insects such as ants and other hymenopterous insects.

This invention further relates to an aerosol stable foam bait composition useful in controlling cockroaches, silverfish and other crawling insects.

Weil et al U.S. Pat. No. 3,361,624 discloses a method for destroying pests which comprises applying a pesticide to the locus of the insect. The compound is placed in an attractant and carried to the colony of the social insects where it destroys the colony by use of a delayed toxicant. There is no mention in Weil of the use of a toxicant and attractant in an edible foam carrier which is adaptable for use in crevices such as the present invention which, upon application, expands and coats all the surfaces of the crevice with the pesticide and then contracts, offering an edible surface which is suitable for transportation of the toxicant back to the insect colony or for the direct contact kill of the insect. Thus, the present invention differs from Weil et al.

Geary U.S. Pat. No. 3,076,744 relates to a substantially homogeneous insecticidal bait which is mixed with an attractant to facilitate ingestion of the pesticide by the insect. Geary makes no mention of a foam carrier, such as is disclosed herein, and accordingly it is believed that the present invention differs from Geary.

Margot U.S. Pat. No. 3,030,267 relates to a method of detecting infestation of Mediterranean fruit flies. The compound of Margot is both an attractant and an insecticide which appears to be specific for fruit flies only. The present invention differs from Margot in that the foam of the present invention acts as a carrier for the pesticide and the attractant and therefore can be used with both crawling insects as they crawl over the foam and those insects which are attracted to the bait in the foam.

Himel et al U.S. Pat. No. 4,286,020 relates to a composition for the inflight encapsulation of particles such as particles of insecticides. Himel is pertinent in that the encapsulation of the particles is by way of a polyvinyl ethers, and polyvinyl acetate and certain interpolymers. These resemble the film forming polymers of the present invention used as a foam support. However, there is no disclosure of the edible film forming foam carrier of the present invention combined with attractants and insecticides which are essential to the operation of the present invention. According, it is believed that the present invention differs from Himel.

A publication entitled "U.S.D.A. Stored Product Insect Research and Development Preliminary Evaluation and Formulation of Chemicals as Insecticides, Repellents and Attractants" teaches a toxicant which shows promise of direct contact and residue toxicity against certain flies. There is, however, no teaching in this publication of a foam carrier for the toxicant and an attractant within the foam carrier which induces insects or other pests to ingest the foam or carry it back to the nest where the toxicant may have effect. Thus, the present invention differs from the U.S.D.A. publication.

SUMMARY OF THE INVENTION

This invention consists of an aerosol stable foam insect bait composition suitable for crawling insects, which comprises a film forming edible foam carrier, present in an amount of about 0.5% to 10% by weight of the total composition, an and attractant which is suitable to be carried by the foam carrier, present in an amount of about 0.1 to 10% by weight of the composition. The attractant should be such as to be specific to the insect to be attracted. Specifically, if the insect to be attracted is attracted to sugars, a sugar composition may be used as the attractant. In contrast, if the insect is attracted to vegetable oils, animal fats, and proteinaceous materials, such should be incorporated as an attractant. These are not seen to be limiting, rather they are to be directed to the recognition that various insects feed upon various food sources and the attractant should be such as to attract the widest possible range of target insects to the edible foam carrying the toxicant.

A toxicant is present in the foam carrier in an amount of about 0.01 to 10% by weight of the composition. The toxicant should be a non-repellent toxicant or, in the alternative, if a toxicant is chosen which exhibits a repellency, that repellency should be such as to be able to be overcome by the attractant found in the foam carrier. A toxicant can be formulated that exhibits either delayed toxicity which is useful in controlling social insects or may exhibit a very rapid effect which may each be effective in controlling non-social crawling insects. In addition, various insect growth regulators may each be incorporated as a toxicant which, when ingested by the insect, interrupts a certain phase of its development whereby it may be rendered sterile, immature or unable to molt, or the regulator may cause some other deficiency in metabolism whereby insect viability is imperiled.

Inasmuch as it is contemplated that this composition should be in an aerosol form, a propellent which may preferably be a hydrocarbon or a fluorocarbon may be used, and the balance of the composition is comprised of water.

The composition is such as to be pressurized within an aerosol can for application along cracks and crevices and other inaccessible places where insects are apt to hide.

Upon application, the foam carrier expands into a foamy bead which coats all surfaces of the crack to which it is applied with toxicant and attractant. Upon drying, the foam carrier contracts presenting an edible film along the crevice which is attractive to the insects. The insects ingest the foam which then allows the toxicant to have its desired effect, i.e. either delayed or immediate. Moreover, the toxicant should be such that even if the insect does not ingest it but rather merely comes in contact with it, the desired effect is had.

It is an object of this invention to present an aerosol stable foam bait for crawling insects which is water soluble and is useful against insects which come in contact with the bait.

It is another object of this invention to provide an aerosol stable foam bait composition for crawling insects, which presents an attractant which encourages the insect pests to ingest the edible foam and also the toxicant thereby eradicating the insect pests.

It is another object of this invention to present an aerosol stable foam bait composition for crawling insects, which has an attractant and a toxicant exhibiting delayed toxicity which is useful in controlling social insects such as ants or other hymenopterous insects by encouraging the insect to carry pieces of the foam with the toxicant back to the nest where the colony may be eradicated.

Other objects will become apparent to those skilled in the art by reading the description detailed of the preferred embodiments.

DETAILED DESCRIPTION OF THE PREFERRED EMBODIMENTS

The aerosol stable foam bait composition, of the present invention, for crawling insects is comprised of a self forming edible foam carrier, an attractant suitable to be carried by the foam carrier which is specific to the type of insect to be controlled, and a toxicant compatible with the foam carrier.

The composition is pressurized within a container with a suitable propellent which is preferably a hydrocarbon or fluorocarbon but may also be a compressed gas such as nitrogen or carbon dioxide or dimethyl ether propellent. The composition is suitable to be applied into crevices or cracks and the like where it expands to fill the crevice thereby coating the crevice with the foam toxicant. Upon drying, the foam contracts and forms a film on all surfaces of the crevice. When insects crawl over the crevice or ingest the foam, they come in contact with the toxicant which then has the desired effect: eradicating the insect pests.

The aerosol foam is comprised of a preferably water soluble film forming polymer which is present in an amount of about 0.5% to 10% by weight of the composition. The polymer may be selected from the group consisting of polyvinyl alcohol, polyvinyl pyrrolidone, polyvinyl acetate, and the like. The foam is preferably water soluble so that it may be easily cleaned up after it has had its desired effect.

An emulsifier is also included in the invention to emulsify the film forming polymer so that it will foam. The emulsifiers are surfactants and are present in the composition in amounts of about 0.01% to 5% by weight of the composition, and preferably 0.1 to 2.0% by weight of the composition. The emulsifiers are water soluble and may be selected from the group consisting of sucrose ester, ethoxylated glycols, alcohols, carboxylic acids, amines, sorbitol derivatives, organosulfates, organosulfonates, phosphate esters, amine oxides and the like. The only limitations on the emulsifier are that it emulsify the film forming polymer and facilitate its foaming upon release from the pressurized can and that the emulsifier not interfere with attraction of the insect.

The foam bait of the present invention is provided with an attractant which is compatible with the foam and specific to the type of insect to be controlled. In this regard, if the insect to be controlled is attracted by oils or lipids or some proteinaceous material, such bait could be incorporated into the foam. In the alternative, if the insect is attracted to sucrose or other sugars, such as maltose, fructose, galactose and the like, such could be incorporated into the formulation as well. Moreover, it is also conceivable to incorporate both forms of attractant inside the bait thereby providing for a foam insect bait composition which attracts all types of insects and is not subject to seasonal variations in regard to attracting insects.

The stable foam bait composition of the present invention also includes toxicants which may have either a delayed toxicity which is useful in controlling social insects such as ants, or it may have a more immediate effect which may be desirable when controlling crawling insects such as cockroaches, crickets and the like. The toxicants may be selected from the group consisting of organophosphorus compounds, carbamates, insect growth regulators (IGR's) and inorganic toxicants.

The organophosphorus compounds are selected from the group consisting of phosphates, phosphorothioates, phosphorothionates and the like. Examples are O-O-Diethyl-O-(3,5,6-trichloro-2-pyridyl) phosphorothioate known under the tradename chlorpyrifos, O-O-Diethyl-O-(2-isopropyl-6-methyl-5-pyrimidinyl) phosphorothioate known under the tradename diazanon, O-O-Dimethyl-O-(3-methyl-4-nitrophenyl) phosphorothioate known under the tradename fenitrothion, 2-Diethylamino-6-methylpyrimidin-4-yl dimethyl phosphorothioate known under the tradename pirimiphos methyl, O,O-Dimethyl-O-(3-methyl-4-(methylthio)phenyl) phosphorothioate known under the tradename fenthion, (Diethoxy-thiophosphoryloxyimino)phenyl acetonitrile known under the tradename phoxim, O,S-Dimethyl acetylphosphoramidothioate known under the tradename acephate, O-2-methylcarbonyl-1-propenyl O,O-dimethyl phosphorothioate known under the tradename methacrifos, and the like.

The carbamates may be selected from the group consisting of 2-(1-methylethoxy)phenyl methylcarbamate known under the tradename propoxur, 2,2-Dimethyl-1,3-benzodioxol-4-yl methyl carbamate known under the tradename bendiocarb, 2-(1,3-dioxolan-2-yl)phenyl methylcarbamate known under the tradename dioxacarb, 1-napthyl methylcarbamate known under the tradename carbaryl, and the like.

The inorganic toxicants may be selected from the group consisting of boric acid, sodium borate, silica gel, arsenic compounds, and the like.

The insect growth regulators which may be incorporated into the foam carrier of the present invention include methoprene Isopropyl (E,E)-11-methoxy-3,7,11- trimethyl-2,4-dodecadienoate and hydroprene Ethyl (E,E)-3,7,11-trimethyl-2,4-dodecadienoate. By the use of insect growth regulators, it may prove possible to interrupt the life cycle of the insects, particularly cockroaches, thereby rendering them infertile or sterile. Thus, the use of this type of toxicant would have its desired effect in a long term fashion whereby the insects, unable to propagate, would decline in population.

The only restriction to be placed on the toxicants used in the present invention is that they should not be repellent to the insects to be controlled. Thus, pyrethroids are not expected to perform well due to their repellency action.

The propellent may be selected from the group consisting of hydrocarbons or fluorocarbons or even, in some cases, carbon dioxide or dimethyl ether. The propellent should be present in an amount of about 4% to 15% depending upon the amount of pressurization needed in the container.

The amount of water present in the composition should vary from about 70% to about 90% in order to dissolve the polymer while it is being held in solution in the can. At any rate, the widest possible range should be given to this constituent inasmuch as it should be tailored to fit the needs of each individual application.

In the preparation of the aerosol foam bait insecticide of the present invention, toxicant to be used is blended with the surfactant if the surfactant is an oil. If the surfactant is in solid form, the surfactant should be melted if possible, to facilitate mixing with the toxicant.

The toxicant/surfactant mixture is then added during agitation to a solution of a water-soluble polymer such as polyvinyl alcohol, and stirring is continued until the mixture is homogeneous. The attractant is then dissolved in water and added to the toxicant/surfactant polymer solution with moderate stirring. The resulting aqueous solution is pressurized with an appropriate aerosol propellent in a suitable aerosol package such as is standard in the art. It may also be desirable to equip the package with a crack-and-crevice applicator such as may be found in the prior art.

From this disclosure, it can be seen that the aerosol foam bait insecticide of this invention may be made by combining a toxicant, in an amount sufficient to have the desired effect, with an aerosol foam which is made of a film forming polymer compatible with the toxicant and containing an emulsifier sufficient to cause the polymer to foam, and an attractant with the balance water. A propellent sufficient to pressurize the formula in a container is added to allow for aerosol application of the invention.

The following examples are offered to illustrate the inventive concept of the aerosol stable foam roach bait composition and are not intended to be limiting in the scope and spirit of the present invention.

EXAMPLE I

The following five spray bait variables were prepared in accordance with the preparation as detailed above. They were compared as to efficacy on German cockroaches, American cockroaches and ants.

TABLE I

| INGREDI-ENTS | 1 | 2 | 3 | 4 | 5 |
|---|---|---|---|---|---|
| Dursban MC | 0.95 | 0.95 | 0.95 | 0.95 | 0.95 |
| (+)-Maltose | 4.00 | 4.00 | 4.00 | 4.00 | 4.00 |
| Myristic Acid | 1.00 | — | — | — | — |
| Triethanolamine | 0.70 | — | — | — | — |
| Clindrol 100 LM | 0.30 | — | — | — | — |
| Vinol 325, 5% | — | — | 40.00 | 40.00 | — |
| Crodesta SL-4 | — | 1.00 | — | 1.00 | — |
| Atlox 3409F | — | — | 1.00 | — | 1.00 |
| Joncryl 74F | — | 40.0 | — | — | — |
| Zinc Oxide Solution | — | 3.00 | — | — | — |
| Water | 83.05 | 41.05 | 44.05 | 44.05 | 84.05 |
| A-46 | 10.00 | 10.00 | 10.00 | 10.00 | 10.00 |
| | 100.00% | 100.00% | 100.00% | 100.00% | 100.00% |

Formula 3 and 4 both performed well as residual applications against *Blatella germanica* providing 100% mortality at 24 hours in the test performed. Upon application, the foam would fill cracks and crevices and upon drying leave those areas open. This would allow entry and thus contact by the pest species. The phagostimulatory properties imparted by, in this case, the maltose, enhance the quality of contact by the insect pests, thereby increasing efficacy.

For use of these formulations against ants it is expected that a lower level of toxicant would be used than for cockroaches so that a slower kill would be the result. In this way the entire colony would be killed rather than only the foraging workers.

Table II indicates the field ant morality choice test using the formulations as indicated above.

TABLE II

| Samples | TIME, HOURS | | | | | | | | |
|---|---|---|---|---|---|---|---|---|---|
| | 0.33 | 1 | 2 | 3 | 4 | 5 | 7 | 9 | 10 |
| 1 | 5.0a | 7.5a | 7.5a | 12.5a | 27.5a | 57.5a | 80a | 92.5a | |
| 2 | 2.5a | 25.0a | 87.5c | 95.0b | 100b | 100b | 100b | 100b | 100 |
| 3 | 7.5a | 22.5a | 47.5a | 97.5b | 100b | 100b | 100b | 100b | 100 |
| 4 | 7.5a | 30.0a | 92.5c | 100b | 100b | 100b | 100b | 100b | 100 |
| 5 | 5.0a | 22.5a | 80.0bc | 100b | 100b | 100b | 100b | 100b | 100 |
| Blank 1 (w/o Dursban) | 0 | 0 | 0 | 0 | 0 | 0 | 0 | 0 | 0 |
| Room Control | | 0 | 0 | 0 | 0 | 0 | 0 | 0 | 0 |

Each number is a mean mortality percentage representing the results of four replicates. Ten ants were used per replicate. a.b.c.=means followed by different letters are significantly different ($P=0.05$, LSD Test); read differences in a columnwise direction only.

Bran and honey mixtures were offered to the ants as a food choice

EXAMPLE II

An arena test is described testing the attractancy and performance of the aerosol stable foam bait for cockroaches *Blatella germanica*. The arena was designed to be large enough to allow kill by ingestion, i.e. there was no forced exposure. There were five (5) replicates per sample and twenty (20) male *Blatella germanica* per replicate.

The roaches were allowed to acclimate to the tray arena and two (2) untreated hides for approximately 18 hours before treated hides were introduced. Food and water was available during the test and the roaches were allowed free choice as to food sources.

The knockdown times were determined at ½ hour intervals up to 4 hours, and again at 24 hours when the residual age was 0.5 hours, to simulate fresh applications, and when the residual age was three days, to simulate a dried mature application.

This test was applied to the following formulations:

|  | FORMULATIONS | | | |
|---|---|---|---|---|
| INGREDIENTS | 1 | 2 | 3 | 4 |
| Dursban MC | 0.95 | 0.95 | 0.95 | 0.95 |
| Vinol 325, 5% | 40.00 | 40.00 | 40.00 | 40.00 |
| (+)-Maltose | 4.00 | 4.00 | 4.00 | 4.00 |
| Water | 46.05 | 46.05 | 46.05 | 46.05 |
| Pluronic L62 | 1.00 | | 1.00 | |
| Crodesta SL-40 | | 1.00 | | 1.00 |
| A-31 | | | 8.00 | 8.00 |
| A-46 | 8.00 | 8.00 | | |
| | 100.00% | 100.00% | 100.00% | 100.00% |

The results of the effectiveness of formulations is contained in Table III.

TABLE III

| Residual Age ½ hr. | Deposit Avg. gm/hide | Avg. % Mortality in Hours | | | | | | | |
|---|---|---|---|---|---|---|---|---|---|
| | | 0.5 | 1.0 | 1.5 | 2.0 | 2.5 | 3.0 | 3.5 | 4.0 | 24 |
| 6230D2-1 | 0.64 | 0 | 1 | 4 | 8 | 9 | 12 | 14 | 19 | 76 |
| -2 | 0.45 | 0 | 1 | 17 | 41 | 46 | 62 | 68 | 78 | 100 |
| -3 | 0.52 | 0 | 1 | 8 | 10 | 16 | 20 | 21 | 24 | 80 |
| -4 | 0.35 | 0 | 5 | 16 | 31 | 42 | 54 | 62 | 67 | 99 |
| Control | — | 0 | 0 | 0 | 0 | 0 | 0 | 0 | 0 | 0 |
| 3 Days | | | | | | | | | | |
| 6230D2-1 | | 0 | 0 | 0 | 0 | 0 | 0 | 3 | 7 | 93 |
| -2 | | 0 | 0 | 0 | 5 | 12 | 21 | 26 | 43 | 99 |
| -3 | | 0 | 0 | 0 | 1 | 1 | 3 | 5 | 8 | 87 |
| -4 | | 0 | 0 | 0 | 3 | 7 | 12 | 21 | 39 | 98 |
| Control | | 0 | 0 | 0 | 0 | 0 | 0 | 0 | 0 | 0 |

These results show that the fresh treatment of formulas 2 and 4 with Crodesta SL-40 were the most effective and attractive bait formulations based on the time required to produce mortality. These treatments showed the same general trend of activity after they were allowed to dry for three days, except that the initial mortality response (i.e., 1-4 hours) was slower.

Observations of the dried residue revealed that a fiberous, web-like deposit remained with −2 and −4 and a flat, transparent (essentially invisible) residue was produced with −1 and −3. This fiberous, web-like texture could possibly be a significant contributing factor toward the faster activity of samples −2 and −4 because more bait surface area is available for the cockroach to feed on.

KEY TO TABLES I AND III

Clindrol 100 LM=Alkanol amide, trademark of Clintwood Chemical Company
Vinol 325, 5%=polyvinyl alcohol, trademark of Air Products Company
Crodesta SL-40=Sucrose monococoate, trademark of Croda Inc.
Atlox 3409F=Blend of anionic and nonionic emulsifiers alkyl aryl sulfonate/nonionic surfactant, trademark of ICI Americas
A-46=Blend of isobutane/propane 70:30
A-31=Isobutane
Pluronic L62=Propylene ethoxylated, propylene oxide, propylene glycol condensate, trademark of BASF

I claim:

1. A stable-foam insect-bait aerosol composition, adapted to be applied into a crevice or a crack, for controlling the populations of crawling insects selected from the group consisting of ants, cockroaches, crickets and silverfish, the insect-bait aerosol composition comprising:
   an insect attractant, present in an amount of about 0.1 to about 10% by weight of the insect-bait composition;
   an insect toxicant, present in an amount of about 0.01 to about 10% by weight of the insect-bait composition;
   an insect-edible, foamable, film-forming polymeric carrier, selected from the group consisting of polyvinyl alcohol, polyvinyl pyrrolidone, and polyvinyl acetate and present in an amount of from about 0.5 to about 10% weight of the insect-bait composition, for carrying both the attractant and the toxicant, the film-forming carrier being characterized as being adapted to be applied into the crevice or the crack and as being able to form a insect-edible foam matrix therein, both the attractant and the toxicant being contained within the insect-edible foam matrix, the crevice-applied or crack-applied foam matrix being characterized as initially expanding and thereafter contracting thereby presenting an insect-edible surface which is accessible to the crawling insect, the population of which is to be controlled;
   an effective amount of an insect-edible, water-soluble emulsifier, for emulsifying the film-forming polymeric carrier thereby enabling the foamable polymeric carrier to form the insect-edible foam matrix:
   an effective amount of a propellent, for causing the emulsified, foamable, film-forming polymeric carrier to form the insect-edible foam matrix; and
   water, present in an amount of up to about 90% by weight of the insect-bait composition.

2. The aerosol composition of claim 1 wherein the attractant is selected from the group consisting of a sugar, together with one of an oil or a lipid of a proteinaceous material, and combinations thereof.

3. The aerosol composition of claim 2 wherein the sugar is selected from the group consisting of sucrose, maltose, fructose, and galactose.

4. The aerosol composition of claim 1 wherein the toxicant is selected from the group consisting of an organophosphorus compound, a carbamate, an insect growth regulator, and an inorganic toxicant.

5. The aerosol composition of claim 1 wherein the emulsifier is present in an amount of about 0.1 to about 2.0% by weight of the insect-bait composition.

6. The aerosol composition of claim 1 wherein the emulsifier is selected from the group consisting of a sucrose ester, an ethoxylated glycol, an alcohol, a carboxylic acid, an amine, a sorbitol derivative, an organosulfate, an organosulfonate, a phosphate ester, and an amine oxide.

7. The aerosol compositions of claim 1 wherein the propellent is selected from the group consisting of a hydrocarbon, a fluorocarbon, and a compressed gas.

8. The aerosol composition of claim 7 wherein the compressed gas is selected from the group consisting of nitrogen, carbon dioxide, and dimethyl ether.

* * * * *

UNITED STATES PATENT AND TRADEMARK OFFICE
CERTIFICATE OF CORRECTION

PATENT NO. : 4,889,710

DATED : December 26, 1989

INVENTOR(S) : John D. Hagarty

It is certified that error appears in the above-identified patent and that said Letters Patent is hereby corrected as shown below:

In the ABSTRACT, lines 9-10, please substitute "intersurface" with
-- inner surface --.

At column 1, line 8, please substitute "34 U.S.C. § 120" with
-- 35 U.S.C. § 120 --.

At column 2, line 16, please substitute "an and attractant" with
-- and an attractant --.

At column 3, line 17, please substitute "the description detailed" with
-- the detailed description --.

At column 4, line 23, please substitute "diazanon" with
-- Diazinon --.

Signed and Sealed this

Fourth Day of December, 1990

Attest:

HARRY F. MANBECK, JR.

*Attesting Officer*      *Commissioner of Patents and Trademarks*